(12) United States Patent
Odermatt et al.

(10) Patent No.: US 6,592,823 B1
(45) Date of Patent: Jul. 15, 2003

(54) SENSOR FOR DETECTING THE INSTANTANEOUS CONCENTRATIONS OF A PLURALITY OF GAS CONSTITUENTS IN A GAS

(75) Inventors: Peter Odermatt, Bad Dürkheim (DE); Andreas Spiegel, Ludwigshafen (DE); Jürgen Dittrich, Baden-Baden (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/412,597

(22) Filed: Oct. 6, 1999

(30) Foreign Application Priority Data

Oct. 9, 1998 (DE) ............................................. 198 46 487

(51) Int. Cl.[7] ................................................. G01N 30/96
(52) U.S. Cl. ............................ 422/88; 422/83; 422/94; 422/98
(58) Field of Search ............................. 422/88, 98, 90; 60/286; 436/178, 151; 423/239.1, 213.2; 427/372.2

(56) References Cited

U.S. PATENT DOCUMENTS

| | | | |
|---|---|---|---|
| 4,608,232 A | * | 8/1986 | Sunano et al. ............... 422/88 |
| 4,985,126 A | * | 1/1991 | Haefele et al. ........... 205/779.5 |
| 4,992,384 A | * | 2/1991 | Laurs et al. ................ 436/151 |
| 5,064,693 A | * | 11/1991 | Hayakawa et al. ....... 427/372.2 |
| 5,093,269 A | * | 3/1992 | Leichnitz et al. ........... 436/178 |
| 5,334,350 A | * | 8/1994 | Friese et al. .................. 422/98 |
| 5,352,353 A | | 10/1994 | Schoenauer et al. |
| 5,372,785 A | * | 12/1994 | Johnson et al. ............... 422/90 |
| 5,397,442 A | | 3/1995 | Wachsman |
| 5,543,124 A | * | 8/1996 | Yokota et al. ............ 423/239.1 |
| 5,635,136 A | * | 6/1997 | Glaunsinger et al. ......... 422/88 |
| 5,676,912 A | * | 10/1997 | Sharma et al. ........... 423/213.2 |
| 5,759,493 A | * | 6/1998 | Raisanen ..................... 422/98 |
| 6,022,464 A | | 2/2000 | Schumann |
| 6,058,576 A | * | 5/2000 | Harris ........................ 73/29.01 |
| 6,069,013 A | * | 5/2000 | Plog et al. ................... 436/113 |
| 6,122,909 A | * | 9/2000 | Murphy et al. ................ 60/286 |
| 6,153,072 A | * | 11/2000 | Inoue et al. ................. 204/425 |
| 6,238,536 B1 | * | 5/2001 | Lundgren et al. ........... 204/426 |
| 6,319,724 B1 | * | 11/2001 | Lewis et al. ................. 436/149 |
| 6,331,244 B1 | * | 12/2001 | Lewis et al. ............. 205/777.5 |
| 6,350,369 B1 | * | 2/2002 | Lewis et al. ............. 205/777.5 |
| 6,361,754 B1 | * | 3/2002 | Peter-Hoblyn et al. .. 423/213.2 |

FOREIGN PATENT DOCUMENTS

| | | |
|---|---|---|
| DE | 36 10 363 | 10/1987 |
| DE | 36 10 364 | 10/1987 |
| DE | 41 09 516 | 8/1992 |
| DE | 44 42 272 | 5/1996 |
| DE | 196 10 911 | 9/1997 |
| DE | 196 23 434 | 12/1997 |
| DE | 196 51 328 | 6/1998 |
| DE | 197 34 861 | 3/1999 |
| DE | 197 57 112 | 4/1999 |
| WO | WO 95/09361 | 4/1995 |
| WO | WO 95/30146 | 11/1995 |

OTHER PUBLICATIONS

E. Haefele, et al., Sensors and Actuators, B. 4, pp. 529–531, "Measurement of Ammonia with the Solidox–$NH_3$ System", 1991.

E. Haefele, et al., Sensors and Actuators, B. 4, pp. 525–527, "Application of the $ZrO_2$ Sensor in Determination of Pollutant Gases", 1991.

H. Klingenberg, Automobile Exhaust Emission Testing, pp. 358–360, "Vehicle Exhaust Emission Testing Procedures—Overview and Criticism", 1996.

* cited by examiner

Primary Examiner—Jill Warden
Assistant Examiner—Brian Sines
(74) Attorney, Agent, or Firm—Oblon, Spivak, McClelland, Maier & Neustadt, P.C.

(57) ABSTRACT

A sensor for detecting the instantaneous concentrations of a plurality of gas constituents of a gas, which contains a first zone in which the instantaneous concentration of oxygen is measured, a second zone in which the instantaneous concentration of $NH_3$ is measured, and a third zone in which the instantaneous concentration of NO is measured.

13 Claims, 2 Drawing Sheets

SENSOR FOR DETECTING THE INSTANTANEOUS CONCENTRATIONS OF A PLURALITY OF GAS CONSTITUENTS IN A GAS

The invention relates to a sensor for detecting the instantaneous concentrations of a plurality of gas constituents in a gas, in particular for exhaust-gas measurement, and combustion exhaust gases from incineration plants for fossil or biological fuels or waste or from combustion engines. For example, automobile engines operating on the diesel principle contain harmful substances which represent environmental pollution. In particular, nitrogen oxides, as toxic and environment-endangering substances, are at the center of public interest and should be removed as completely as possible from the combustion exhaust gases in order to avoid environmental pollution. Examples of such nitrogen oxides are NO, $NO_2$, $NO_3$, $N_2O_3$, $N_2O_4$ and $N_2O_5$. These are known from the textbook literature, but NO and $NO_2$ are of particular importance.

A diesel exhaust gas can, according to the reference Kraftfahrtechnisches Taschenbuch, Robert Bosch GmbH, 1991, p. 513, have the following compositions:

| | |
|---|---|
| $NO_x$ | 50–2500 ppm |
| HC | 50–500 ppm $C_1$ |
| CO | 100–2000 ppm |
| soot | 20–200 mg/m$^3$ |
| $H_2O$ (steam) | 2–11 vol % |
| $O_2$ | 2–18 vol % |
| $CO_2$ | 0–16 vol % |
| $N_2$ | remainder |

HC denotes hydrocarbons, $H_2O$ is in the form of steam, and the concentrations are based on volumes. The temperature is 100–750° C., and the pressure, which is not quoted, is assumed to be from 1 to 1.05 bar. $SO_2$ may additionally be present.

The nitrogen oxides $NO_x$ are frequently reduced using ammonia or ammonia-releasing substances, such as urea, ammonium carbonate, ammonium hydrogen-carbonate, ammonium cyanate and others. Urea can be fed in, for example, in a 30% strength aqueous solution, and $NH_3$ in the form of a gas. The reduction proceeds in accordance with the following reaction equations:

$$4\ NO + 4\ NH_3 + O_2 \rightarrow 4\ N_2 + 6\ H_2O$$

$$NO + NO_2 + 2NH_3 \rightarrow 2\ N_2 + 3\ H_2O$$

$$2\ NO_2 + 4\ NH_3 + O_2 \rightarrow 3\ N_2 + 6\ H_2O$$

In order to convert the nitrogen oxides as completely as possible, an equimolar or higher proportion of ammonia is advantageously added. The molecular weights are 17 for $NH_3$, 46 for $NO_2$, 62 for $NO_3$ and 54 for $(N_2O_5)/2$. For a stoichiometric reaction, about three times the proportion by weight or a single proportion by volume of ammonia, based on $NO_x$, is needed. If a 3% excess of ammonia is assumed with the abovementioned composition with on average 2000 ppm of $NO_x$, 60 ppm of ammonia remain in the exhaust gas. If this is not to be exceeded, the measurement must still be able to detect 60 ppm with a reliability of 10 ppm. The measurement must still function reliably at exhaust gas temperatures of from 100 to 750° C. Furthermore, soot or ammonium salt dusts must not interfere with the measurements, and the sensor must not be affected by corrosion caused, for example, by sulfur oxides.

Incorrect measurements entail the risk of a relatively large excess of one of the environmental pollutants ammonia or nitrogen oxide being present in the exhaust gases. Both are very undesired in the environment. Attempts are being made to reduce the concentration of nitrogen oxides to below the legally permissible level and at the same time not to add any excess ammonia.

In DE-A-3 721 572, the nitrogen oxide ($NO_x$) concentration in the exhaust gases of an engine are measured for selective catalytic reduction of $NO_x$ and, depending on the measured $NO_x$ concentration, fed to a catalyst $NH_3$ for conversion. At least 75% of the regulation of the amount of $NH_3$ is effected by the engine load data, while the remainder is regulated depending on the $NO_x$ concentration measured in the exhaust gases. It is hoped that this will improve the sluggish regulation of the $NH_3$ supply known hitherto by measuring the $NO_x$ concentration after the catalyst in non-steady-state operation, where the power and speed of the engine and thus the $NO_x$ concentration in the raw emission from the engine change rapidly. This reaction time is given as about 1 minute, while the addition of ammonia remains constant for a different amount of exhaust gas and a different exhaust-gas composition, since the sluggish sensor has not yet detected the change.

EP-B-0 447 537 furthermore discloses that, for operation of an oxidation catalyst, the $NH_3$ portion must be as low as possible in order to achieve the catalytic action for destruction of dioxins.

The journal "Sensors and Actuators", B4, 1991, page 530, gives a response time of 30 s for the commercial SOLIDOX-$NH_3$ system. Here too, the measurement time is too long for adequate regulation of a non-steady-state operating mode.

U.S. Pat. No. 2,310,472 discloses analyzing automobile exhaust gases by burning them catalytically and measuring the temperature increase as an increase in the resistance of the combustion catalyst. This is carried out by means of a Wheatstone bridge. The catalyst used is a cerium oxide-coated platinum wire or a filament of catalytic material, such as platinum. The addition of ammonia for the catalytic $NO_x$ reduction of the automobile exhaust gas is not mentioned.

U.S. Pat. No. 2,583,930 discloses analyzing combustible gases or vapors by burning them catalytically. The catalyst proposed is a platinum wire or a platinum/rhodium wire whose change in resistance is measured, again using a Wheatstone bridge. The particular advantage here is the avoidance of drift.

EP-A-0 591 240 discloses a sensor for measuring ammonia. The sensor is sensitive to one gas constituent through a thin layer of platinum or palladium applied to an oxide surface. A combustion reaction, for example, is catalyzed, and the primary signal is the electrical resistance of a semiconductor. At least two sets of electrodes attached to the semiconductor at different distances enable an impairment in the function to be recognized.

U.S. Pat. No. 3,586,486 discloses an analysis of an automobile exhaust gas in which the catalyst employed for the combustion is platinum in the form of a platinum black film in a thickness of 0.0508 mm (0.002 inch). The resistance of the catalytic resistance element depends on the temperature, and the measurement is carried out using a Wheatstone bridge.

The fact that the above-described sensor does not work satisfactorily is noted by U.S. Pat. No. 4,197,089, which proposes a $WO_3$ film as sensor. This is sensitized for $NH_3$ by a small amount of a platinum catalyst. The platinum catalyst is in the form of a thin layer under the $WO_3$ film. The change in resistance is measured by means of a Wheatstone bridge, with the resistance of the $WO_3$ film dropping owing to the reducing agent $H_2S$ or $NH_3$.

DE-A-4 117 143 discloses analyzing the proportion of $NH_3$ in automobile exhaust gases from diesel engines. $NH_3$ is oxidized catalytically, with the increase in the temperature of the gas caused by the evolution of heat being taken as a measure of the $NH_3$ concentration. The catalyst is located within the honeycomb channel, or alternatively a gas substream can be taken. Furthermore, stoichiometric feed of $NH_3$ at constant full-load operation is disclosed, but otherwise cycled, super-stoichiometric addition is the subject matter of this publication.

DE-C-3 543 818 describes how an electrochemical $ZrO_2$ cell functions on this basis for measuring the oxygen concentration in gases. Another, likewise known process for measuring the oxygen concentration is disclosed in an information sheet from Dittrich Elektronik, Bahnhofstrasse 67, 76532 Baden-Baden, which is commercially available together with the oxygen sensors used.

The slowness of the sensors is a recurring problem since too few measurement data or an excessively long measurement time make regulation of the non-steady-state operating mode more difficult.

Significantly shorter reaction times are obtained with a sensor with which the instantaneous concentrations of oxygen, ammonia and nitrogen oxide in combustion exhaust gases are determined simultaneously. In the sensor, three different zones are provided, in one of which the oxygen concentration is measured and in the other two the concentrations of $NH_3$ and NO are measured, preferably on the basis of the oxygen consumption in the partially selective reaction of ammonia or nitrogen oxides and ammonia with oxygen. An increase in temperature caused by exothermic ammonia or nitrogen oxide combustion can also give a measure which is suitable for measurement of the gas concentration. The measurement of small ammonia concentrations is of particular importance here. For example, the ammonia concentration of about 60 ppm present in combustion exhaust gases should be measured continuously with an accuracy of 10 ppm in order that, on the basis of the measurement results, the metering of the ammonia takes place in such a way that significant environmental damage is not caused.

In addition to measurement of $O_2$, $NH_3$ and NO, it may be advantageous to measure the CO concentration in a fourth zone. A suitable catalyst here is, for example, gold.

A particularly suitable sensor is one whose second zone contains a reaction catalyst at least for partially selective reaction of $NH_3$ with $O_2$, whose third zone contains a reaction catalyst at least for partially selective reaction of NO and $NH_3$ with $O_2$ and whose first zone is designed to measure the partial pressure of $O_2$.

The temperature increase can also be set in relation to the ammonia concentration by measuring the heat of combustion on a reaction catalyst, which results, for example, in an increase in the electrical resistance. It can be assumed that the suitable reaction catalysts are electrical conductors whose electrical resistance increases in a readily measurable way with increasing temperature.

The arrangement of the zones on a common substrate has the advantage that the same conditions exist for all three zones. This is particularly important if the substrate is designed to be oxygen-conducting and, together with the zones, delimits gas-filled chambers in which a reference pressure of oxygen has been established. The use of a common substrate establishes in this case uniformity of the oxygen concentrations. This is because the conditions can change along the gas stream. Thus, the content of $O_2$, $NH_3$ and NO is relatively high at the beginning of the catalyst where little reaction has as yet taken place, while the contents toward the end of the catalyst drop considerably, as intended. In accordance with the invention, the contents can be measured closely adjacent to one another at the same point.

In order to prevent sooting of the sensor and to favor dissociation of the oxygen molecule, a heating device may be provided. The heating device is advantageously of such dimensions that a temperature of 500–900° C., preferably 700° C., is achieved in the first to third zones.

A particularly suitable sensor is a construction having a substrate of a material in which $O_2$ can be transported in the form of ions. The substrate is bonded on the one side to a reference layer of a reference material and likewise has on the other side a layer of the reference material, in which chambers are arranged, where the chambers are covered and overall sealed in a gastight manner by sheets of a material in which $O_2$ can be transported in the form of ions, reaction catalysts being arranged on the sheets. Under the action of current, the reference material of the reference layer causes the transport of oxygen in the form of ions through the substrate into the chambers and thus represents a reference quantity for the partial-pressure gradient of the oxygen in the chamber compared with that of the gas stream to be measured. An $O_2$ partial pressure is measured in all three zones.

The sensor is advantageously provided with means for recording the voltage between the reaction catalysts and the reference layer.

The sheets are advantageously fixed to the substrate by means of a glass adhesive. The glass adhesive is not oxygen-conducting, even at the high operating temperatures, and seals the chambers.

The present invention furthermore relates to the use of the sensor according to the invention in a catalyst system in which $NH_3$ is fed in for reduction of nitrogen oxides in combustion gases, where the sensor is arranged at least at the catalyst outlet and/or in the catalyst after the $NH_3$ feedpoint. In addition, a sensor may advantageously also be installed immediately before the catalyst and/or before an $NH_3$ feedpoint. In contrast to the catalyst systems known hitherto, pointwise, reaction-quick measurement of the nitrogen oxides in the combustion gases enables finely metered $NH_3$ feed, so that an excess of $NH_3$ does not exit from the catalyst system.

Thanks to the sensor according to the invention, a further catalyst system can be achieved which, after a $DeNO_x$ catalyst, additionally contains a dioxin-converting catalyst part. The prerequisite for conversion of dioxin in the catalyst is that the $NH_3$ concentration remains below a certain limit.

The $NH_3$ feed is advantageously regulated on the basis of the measurement results from the sensor according to the invention.

The drawing shows an illustrative embodiment of a sensor according to the invention, in which.

Figure 1:
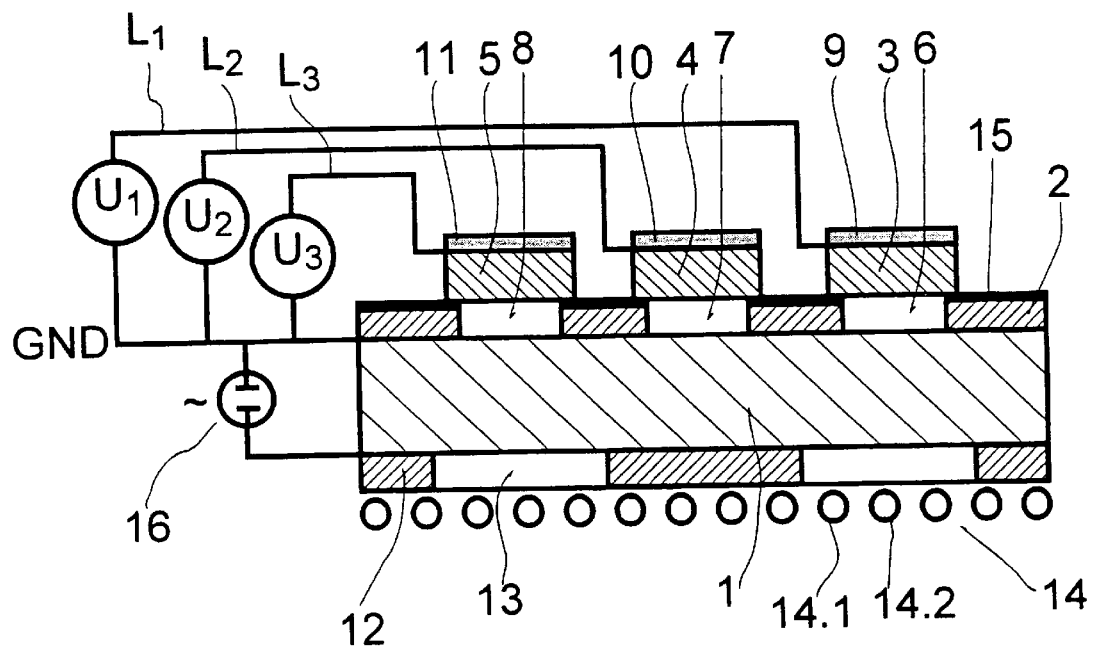
FIG. 1 is a cross section through a sensor.

FIG. 1 shows a 3-zone probe which is suitable as sensor for detection of the instantaneous concentrations of oxygen, $NH_3$ and NO. Starting from a substrate plate 1 of an oxygen-conducting material, here zirconium dioxide $ZrO_2$, a layer 2 of electrically conductive material is arranged on one side. The layer 2 is provided with recesses, which, through the cover sheets 3, 4, 5 placed on the layer 2, form chambers 6, 7, 8 and form the first, second and third zones of the sensor.

Layers 9, 10, 11 consisting of three different materials acting as reaction catalyst are arranged on the cover sheets 3, 4, 5. The reaction catalysts are at least partially selective, i.e. they favour the progress of different reactions.

On the other side of the substrate plate 1 is arranged a further layer 12 of an electrically conducting material, for example the same material as layer 2; care must be taken here to ensure that oxygen can penetrate into the substrate plate.

For this reason, this side of the substrate plate 1 is not completely covered by the layer 12, but instead recesses 13 are present. Finally, a heating device 14 is provided, shown by the heating wires 14.1, 14.2, etc.

In order to measure the voltage difference as the basis for determining the instantaneous concentrations, conductors arranged between the layers 9, 10, 11 and the sheets 3, 4, 5 are provided. The ground conductor, GND, is arranged between the layer 2 and the substrate plate 1.

Furthermore, a current source 16 is provided which enables current flow between the surface of the substrate plate 1 covered with the layer 12 into and out of the chambers 6, 7, 8. As a consequence of the current flow, oxygen partial pressures are established in the chambers 6, 7, 8 which are variable over time, but are always equal to one another in the chambers 6, 7, 8.

The current source 16 is operated in such a way that an upper and lower voltage limit of a voltage $U_1$ is achieved alternately in the oxygen-measuring zone between the layer 9 and the ground conductor 2. The $O_2$ partial pressure in the gas stream is determined using the time difference between the reaching of the limits. This time difference is dependent on the $O_2$ concentration in the exhaust gas. The $O_2$ partial pressure in the chamber 6 itself is insignificant. The reaction time of the sensor is determined by this time interval and depends on the partial-pressure difference of $O_2$ in the chamber 6 and in the gas stream. This difference is about 10–50 mbar at a reaction time of 30–40 milliseconds.

Figure 2:
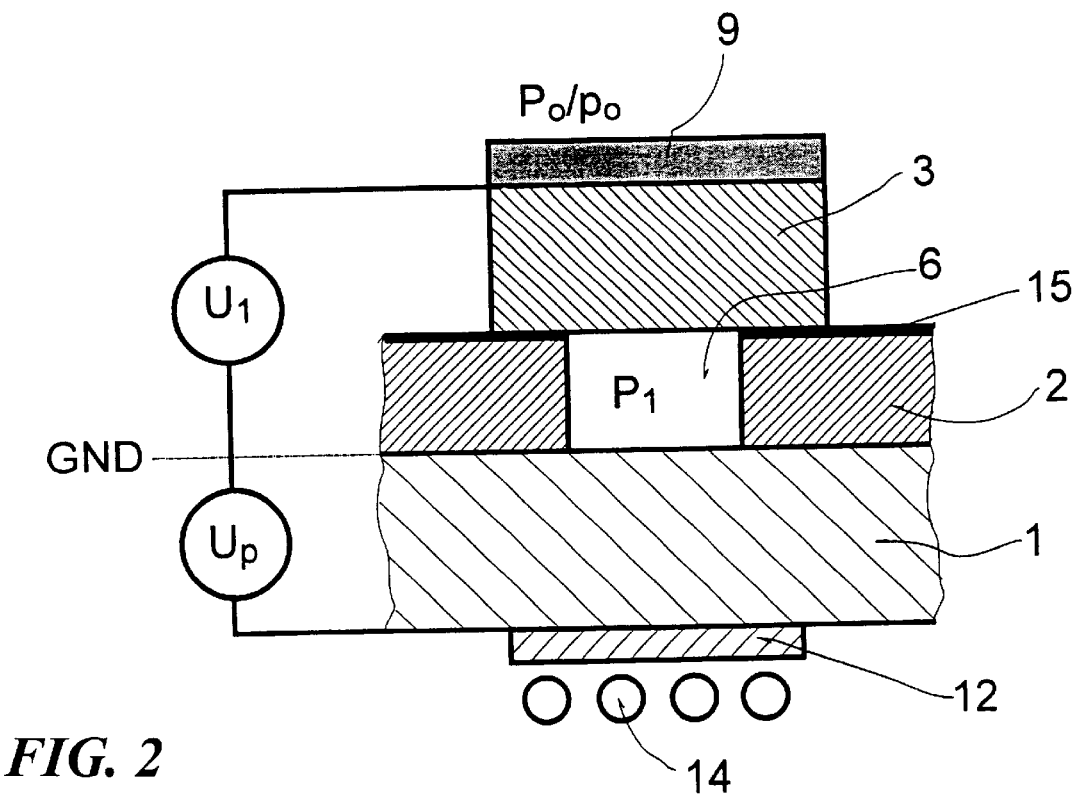
FIG. 2 shows an enlargement of the sensor from FIG. 1.

FIG. 2 shows an enlargement of the first zone of the sensor from FIG. 1. This enlargement illustrates the way in which the individual zones function depending on the material of the coating 9 acting as reaction catalyst. Starting from a certain oxygen concentration in the chamber 6, referred to as partial pressure $p_1$, the voltage difference $U_1$ becomes established at a different oxygen partial pressure $p_0$ as a measure of the concentration prevailing in the gas stream at an ambient pressure of $P_0$.

The voltage difference $U_1$ is measured continuously or at regular intervals by means of a measurement recorder (not shown). Since no current flows, there is no material transport through the sheet 3 of, for example, zirconium dioxide.

The oxygen partial pressure $p_1$ in the chamber 6 is varied within prespecified limits of a pump voltage $U_p$ via the layer 12 as pump conductor, utilizing oxygen-ion material transport, generated under the action of current, through the substrate plate of zirconium dioxide. Use of an appropriate material as catalyst, preferably Pt, results in cleavage of $O_2$ molecules into $O^-$ ions at the pump conductor in accordance with the following equation:

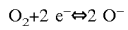

$$O_2 + 2\ e^- \leftrightarrow 2\ O^-$$

The chamber 6 is supplied with oxygen ions through the substrate plate 1, the oxygen ions releasing their electron again when they reach the interface between the chamber and the substrate plate 1 and penetrating into the chamber 6 as oxygen molecules.

The fact that all the chambers 6, 7, 8 have the same oxygen concentration, i.e. the same oxygen partial pressure, allows different voltages $U_1$, $U_2$, $U_3$ (shown in FIG. 1) to be measured for the individual zones if the coatings 9, 10, 11 resulted in different oxygen concentrations. This is achieved by the coating 9, 10, 11 consisting of different reaction catalsyts. In the illustrative embodiment, the reaction catalyst for measurement of the oxygen content is platinum, which causes cleavage of $O_2$ molecules into oxygen ions on the supply of electrons. In order to measure the $NH_3$ concentration, the reaction catalyst used is silver (Ag). In order to measure the NO concentration, the reaction catalyst used is tungsten (W).

Accordingly, different, at least partially selective reactions of NO and of $NH_3$ with $O_2$ take place on the three different reaction catalysts in the first to third zones. Together with the oxygen content measured at this point, the instantaneous concentration of NO or $NH_3$ can be concluded from the oxygen consumption during the conversion reactions with reference to the stoichiometric equations.

The $O_2$ consumption can be calculated from the voltage difference $U_1-U_2$ or $U_1-U_3$ with reference to the reaction equations and the concentration of NO and $NH_3$ in the gas stream can thus be obtained. The absolute $O_2$ partial pressure in the exhaust-gas stream has no significance for this purpose.

For gastight bonding of the plates 3, 4, 5 to the conductor layer 2, use is made of an adhesive 15 which does not conduct oxygen even at 700° C., by means of which the bonding of the plates 3, 4, 5 is likewise carried out. It is essential here that the adhesive 15 remains non-conducting for oxygen even at the operating temperatures of the sensor, which is at about 700° C. A suitable adhesive 15 is a glass powder, which is liquefied by heating after application in powder form to the substrate plate 1 and positioning of the individual components against one another and subsequently forms an impermeable bond on solidification. The adhesive 15 can extend as a layer over the entire surface of the substrate plate 1 or can be arranged only as a bead in the region of the chambers.

By means of the electrical heating, the sensor is heated to temperatures of 500–900° C., preferably 700° C. Since the sensor is very small, this high temperature has virtually no effect on the gas temperature; even if this were the case, it would have no effect on the process.

A suitable material for the conductor layer 2 and the pump conductor 12 is platinum. For measurement of $O_2$, $NH_3$ and NO, the time is measured for $O_2$ transport through the substrate plate into the chambers 3, 4, 5 to a desired $O_2$ partial pressure corresponding to a certain nominal voltage.

Figure 3:
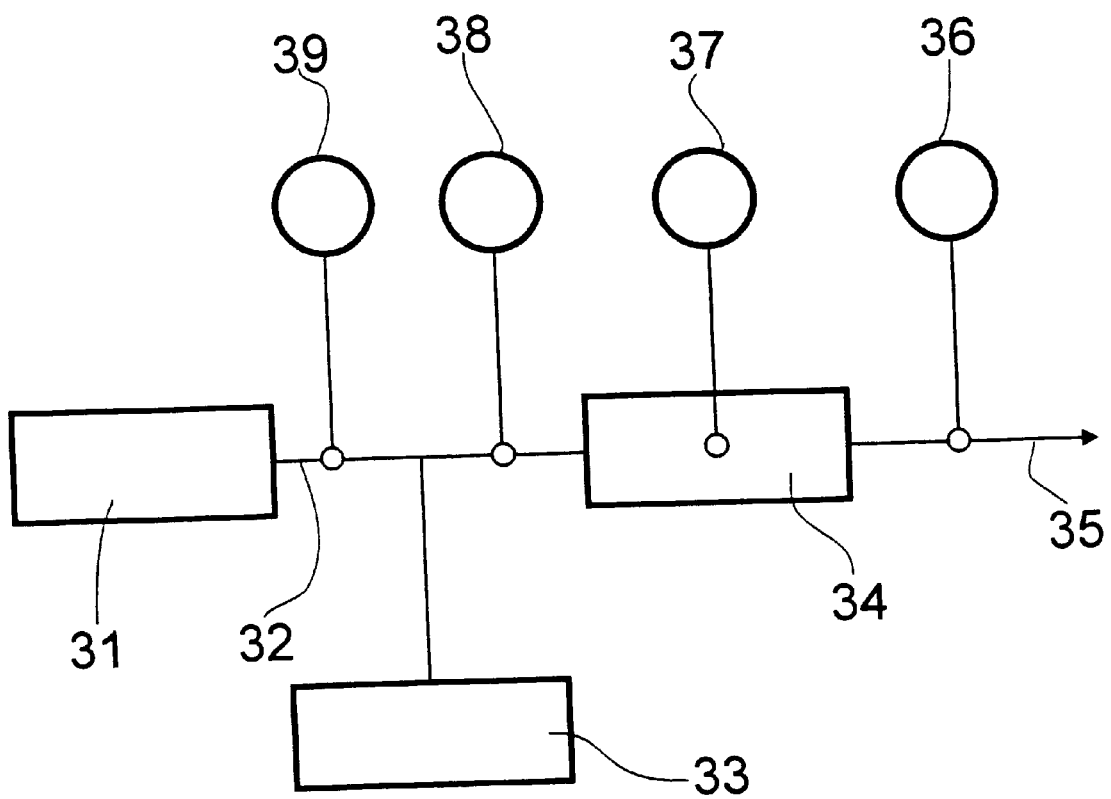
FIG. 3 shows a catalyst system with the sensor according to the invention.

The 3-zone sensor is employed to determine the instantaneous state of the exhaust gas in a $DeNO_x$ catalyst system as shown in FIG. 3. Knowledge of the instantaneous state serves to regulate the ammonia feed with the aim of minimizing the concentrations or amounts of $NH_3$ and NO after exiting the Denox catalyst. Minimization in this case means that the $NH_3$ output and the NO output are below the permissible limit or, as a special case, NO is below the permissible limit and the $NH_3$ output is zero.

Four sensors, as shown in FIG. 3, are sufficient to determine the instantaneous state of the exhaust gas from the catalyst system. $NH_3$ is fed to the exhaust gas 32 exiting a combustion engine 31 by feed of gaseous $NH_3$ or by feed of ammonia-releasing substances from a storage container 33. The exhaust gas with added $NH_3$ enters a catalyst 34, in which the nitrogen oxides $NO_x$ are at least partially reacted with the $NH_3$. The cleaned exhaust-gas stream 35 then leaves the catalyst 34.

The sensor 36 after the Denox catalyst 34 indicates the final state achieved. The sensor 37 in the catalyst 34 (a position after the first third of the catalyst length is preferred) still indicates a value for $NH_3$ and NO which is significantly different from zero and provides information on the action of the catalyst under the conditions of ammonia feed, temperature, catalyst age, etc. prevailing at that moment.

The sensor 38 directly before the catalyst 34 indicates the composition of the exhaust gas and ammonia mixture. The sensor 39 directly after the combustion engine 31 indicates the composition of the exhaust gas 32. At this point, the exhaust gas still contains no ammonia. If the sensor 39 indicates ammonia here, it can only be an $NH_3$-mimicking constituent in the exhaust gas, which must then be subtracted in the subsequent sensors.

In order to achieve the desired aim, the following sensor combinations appear possible:
a) 36,37,38,39
b) 36,37
c) 36,38
d) 37,38
e) 36

In addition to the signals from the sensors 36–39, the engine settings, such as speed and load, and mixture setting can also be used for regulation. The measurements and regulations described can be used for all combustion exhaust gases, in particular for the combustion exhaust gases from internal combustion engines and diesel engines for trucks and automobiles, for gas turbines, coal-fired power stations, garbage incineration-fired power stations, block-type thermal power stations, special-waste incineration plants or tunnel exhaust gases. The invention is particularly advantageous for fast-changing exhasut-gas compositions as occur in non-steady-state driving and operating modes.

For protection against contamination, the sensor is installed in a pipe, which is protected against ingress of solid particles from the gas side in a known manner by means of a sintered metal plate. Since the sensor is heated to a temperature above the sooting point, condensates do not form on the sensor. Owing to the high temperature of the sensor any other residues are burnt, meaning that high functional reliability is ensured.

The 3-zone sensor consists of three zirconium dioxide cells ($ZrO_2$ cells), which, as solid electrolyte, can transport oxygen in the form of ions in a known manner at an elevated temperature of 500–900° C.

The ammonia zone in the 3-zone sensor functions as follows: a thin layer of a catalytic material in which ammonia is reacted with oxygen at 500–900° C. is applied to sheet 4 of zirconium dioxide. This reaction catalyst is, for example, silver. The reaction in this zone takes place in accordance with the following equation:

$$4\ NH_3 + 3\ O_2 \rightarrow 2\ N_2 + 6H_2O \text{ (with Ag)}$$

The underlying ammonia concentration is obtained from the thus-reduced oxygen concentration, measured in comparison to the directly adjacent oxygen sensor.

The nitrogen oxide zone within the 3-zone sensor contains, on sheet 5 of zirconium dioxide, a thin layer of catalytically active material, for example tungsten, on which the reaction of nitrogen oxide with ammonia and oxygen takes place. This takes place in accordance with the following reaction equation:

$$4\ NO + 4\ NH_3 + O_2 \rightarrow 4\ N_2 + 6H_2O \text{ (with catalyst)}$$

The consumption of oxygen on this reaction catalyst, for example tungsten (W), compared with the measurement result of the directly adjacent oxygen sensor, is a measure of the underlying nitrogen oxide concentration.

The two reactions mentioned need not proceed selectively or to 100% on the reaction catalysts, of which Ag and W are mentioned here by way of example. The respective reaction merely needs to proceed to a significantly greater extent. On the silver $NH_3$ reaction catalyst, the other reaction, namely of NO, $NH_3$ and $O_2$, can also take place to some extent. Furthermore, the $NH_3$ oxidation assigned here can also take place to an extent of somewhat less than 100%. Likewise, the reaction of NO, $NH_3$ and $O_2$ on tungsten proceeds merely predominantly. The oxygen consumption, measured as the deficit compared with the measurement result from the oxygen sensor, can be assigned to the concentrations of $NH_3$ and NO by calibration.

The reaction catalysts of the $NH_3$ sensor can be the following: Ag, Pd, Pt, Ru, Ir, In, Ni and $TiO_2$. The reaction catalysts for the NO sensor can be W and $V_2O_5$. These reaction catalysts are applied to the zirconium dioxide in the form of a thin layer. They can be in unconverted form during the reaction, for example as oxide or with adsorbed oxygen.

By combining the three zones to give a 3-zone sensor of small dimensions of approximately 1×1×1 cm, the gas concentrations of oxygen, $NH_3$ and NO are measured at the same time and at the same point. If a plurality of sensors are arranged in a catalyst system, information is obtained on the concentration gradient and the course of the reaction of the exhaust-gas components $O_2$, $NH_3$ and NO along the exhaust-gas stream from the engine outlet to the end of the catalyst. The measurement speed is higher the smaller the volume of the chambers 3, 4, 5 and is in the range from milliseconds to tenths of seconds. The change in the exhaust-gas components with time can also be measured thereby, even in the case of extremely non-steady-state operation. Regulation of the ammonia feed can be carried out directly thereby. The combination of the three zones in a single sensor opens up new opportunities which did not appear possible from the previous prior art.

The sensor according to the invention allows the following problems to be solved:

Since the measurement speed is very fast owing to the small dimensions, the signals can be generated and evaluated within milliseconds to tenths of seconds. Rapid changes in non-steady-state operating mode are recorded immediately.

Since the three gas components $O_2$, $NH_3$ and NO are measured simultaneously and at virtually the same point, the most important reactants in the exhaust gas are known simultaneously.

Since the reference quantity $O_2$ is always likewise measured at the same point as $NH_3$ and NO, even rapid changes in the $O_2$ concentration in the exhaust gas do not result in incorrect measurements.

Since the sensor is small and compact, it can be employed at many points in the exhaust-gas path between the exit of the exhaust gas from the combustion engine and the exit of the cleaned exhaust gas after the catalyst. The change in the exhaust gas along the exhaust-gas path can thus also be recorded. Four measurement points would be advantageous.

The total of 12 signals from four measurement points, 4 each for $O_2$, $NH_3$ and NO, can be evaluated by means of fuzzy logic for regulating the $NH_3$ feed and thus for minimizing the amounts of $NH_3$ and NO.

In order to improve the measurement accuracy of the system as a whole, the sensor 39 can be installed before the $NH_3$ feed in order to detect an $NH_3$ signal mimicked, for example, by hydrocarbons, which can then be taken into account in the subsequent sensors. The sensor necessary for this purpose could be referred to as the comparative sensor.

We claim:

1. A sensor for detecting the instantaneous concentrations of a plurality of gas constituents of a gas, which contains a first zone in which the instantaneous concentration of oxygen is measured, a second zone in which the instantaneous concentration of $NH_3$ is measured, and a third zone in which the instantaneous concentration of NO is measured, wherein the second zone contains a reaction catalyst at least for partially selective reaction of $NH_3$ with $O_2$, and the third zone contains a reaction catalyst at least for partially selective reaction of NO and $NH_3$ with $O_2$.

2. A sensor as claimed in claim 1, wherein a fourth zone is present for measuring the instantaneous concentration of CO.

3. A sensor as claimed in claim 1, wherein the first zone is designed to measure the partial pressure of $O_2$.

4. A sensor as claimed in claim 1, wherein the zones are arranged on a common substrate.

5. A sensor as claimed in claim 1, wherein a heating device is provided.

6. A sensor as claimed in claim 5, wherein the heating device is capable of achieving a temperature of from 500 to 900° C.

7. A sensor as claimed in claim 1, wherein a reference layer of a reference material is bonded to the substrate, the substrate being of a material in which $O_2$ can be transported in the form of ions, a layer of the reference material with chambers is arranged on the other side of the substrate, the chambers are covered and sealed in a gastight manner by sheets of a material in which $O_2$ can be transported in the form of ions, and the reaction catalysts are arranged on the sheets.

8. A sensor as claimed in claim 7, wherein means for recording the voltage between the reaction catalysts and the reference layer over time are provided.

9. A sensor as claimed in either claim 7, wherein a glass adhesive is arranged between the sheets and the substrate.

10. A catalyst system for reducing nitrogen oxides in combustion gases by reaction with $NH_3$, with the sensor as claimed in claim 1 being arranged at least at the catalyst outlet and/or in the catalyst after the $NH_3$ feedpoint.

11. A catalyst system as claimed in claim 10, wherein the sensor is additionally installed immediately before the catalyst and/or before an $NH_3$ feedpoint.

12. A process for minimizing the output of $NH_3$ and NO from a catalyst system as claimed in claim 10, wherein the measurement results from the sensors are used to regulate the $NH_3$ feed.

13. A sensor for detecting the instantaneous concentrations of a plurality of gas constituents of a gas, which contains a first zone in which the instantaneous concentration of oxygen is measured, a second zone in which the instantaneous concentration of $NH_3$ is measured indirectly by measuring the concentration of $O_2$, and a third zone in which the instantaneous concentration of NO is measured indirectly by measuring the concentration of $O_2$, wherein the second zone contains a reaction catalyst at least for partially selective reaction of $NH_3$ with $O_2$, and the third zone contains a reaction catalyst at least for partially selective reaction of NO and $NH_3$ with $O_2$.

* * * * *